US00PP20284P2

(12) United States Plant Patent
de Jong

(10) Patent No.: US PP20,284 P2
(45) Date of Patent: Sep. 8, 2009

(54) ***ASTRANTIA* PLANT NAMED 'STAR OF FIRE'**

(50) Latin Name: *Astrantia hybrid*
Varietal Denomination: Star of Fire

(76) Inventor: Jacobus Robertus de Jong, Westerhout 89, Noordwijkerhout (NL), 2211 TN ( * ) Notice: Subject to any disclaimer, the term of this patent is extended or adjusted under 35 U.S.C. 154(b) by 0 days.

(21) Appl. No.: 12/150,424

(22) Filed: Apr. 28, 2008

(51) Int. Cl.
*A01H 5/00* (2006.01)

(52) U.S. Cl. ..... Plt./408
(58) Field of Classification Search ..... Plt./263, Plt./408
See application file for complete search history.

*Primary Examiner*—Susan B McCormick Ewoldt
(74) *Attorney, Agent, or Firm*—Jondle & Associates, P.C.

(57) ABSTRACT

A new *Astrantia* plant particularly distinguished by its deep red flowers on dark peduncles, large inflorescences and high tolerance to wind and rain, is disclosed.

2 Drawing Sheets

Genus and species: *Astrantia* hybrid.
Variety denomination: 'Star of Fire'.

BACKGROUND OF THE NEW PLANT

The present invention comprises a new and distinct cultivar of *Astrantia,* botanically known as *Astrantia* and hereinafter referred to by the cultivar name 'Star of Fire'. The new cultivar originated from an open pollination made in 2003 in Woubrugge, The Netherlands between the female parent, an unnamed selection of *Astrantia major* (unpatented), and the male parent, an unknown and unnamed selection of *Astrantia* (unpatented). The seeds produced by the open pollination were sown and a single plant selection was chosen for further evaluation and for asexual propagation in 2006 in Woubrugge, The Netherlands.

The new cultivar was created in 2003 in Woubrugge, The Netherlands and has been asexually reproduced repeatedly by division and tissue culture in Woubrugge and De Hoef, The Netherlands, over a two-year period. The present invention has been found to retain its distinctive characteristics through successive asexual propagations.

Plant Breeder's Rights for this cultivar were applied for in the European Union on Oct. 11, 2007. 'Star of Fire' has not been made publicly available more than one year prior to filing of this application.

SUMMARY OF THE INVENTION

The following are the most outstanding and distinguishing characteristics of this new cultivar when grown under normal horticultural practices in Woubrugge and De Hoef, The Netherlands:

1. Deep red flower color;
2. Large inflorescences;
3. Dark peduncles; and
4. High tolerance to wind and rain.

DESCRIPTION OF THE PHOTOGRAPHS

This new *Astrantia* plant is illustrated by the accompanying photographs which show blooms, buds, and foliage of the plant in full color; the colors shown are as true as can be reasonably obtained by conventional photographic procedures. The photographs are of plants that are two-years-old and grown in a field with natural light.

DESCRIPTION OF THE NEW CULTIVAR

Figure 1:
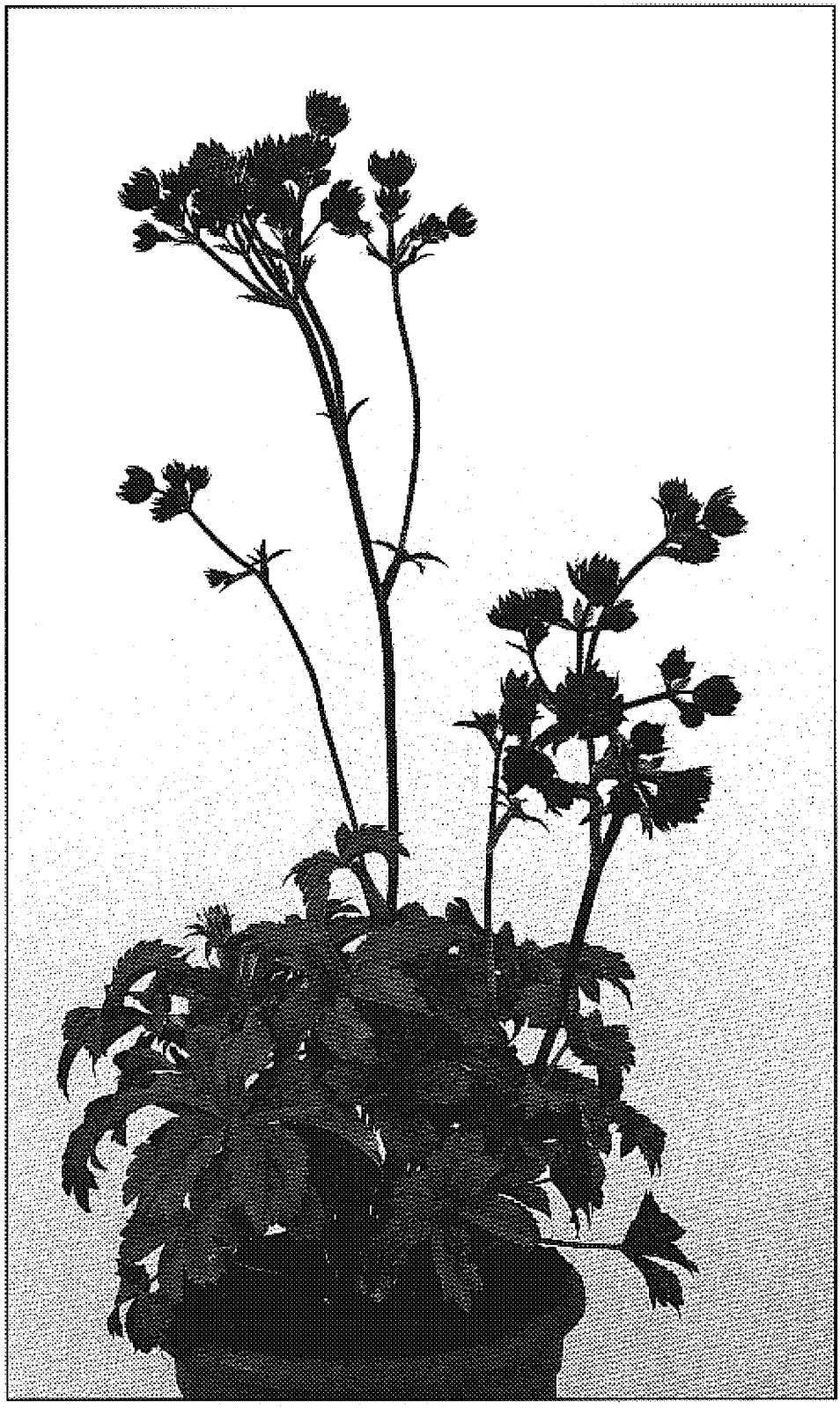
FIG. 1 shows the overall plant habit including blooms, buds, and mature foliage.
Figure 2:
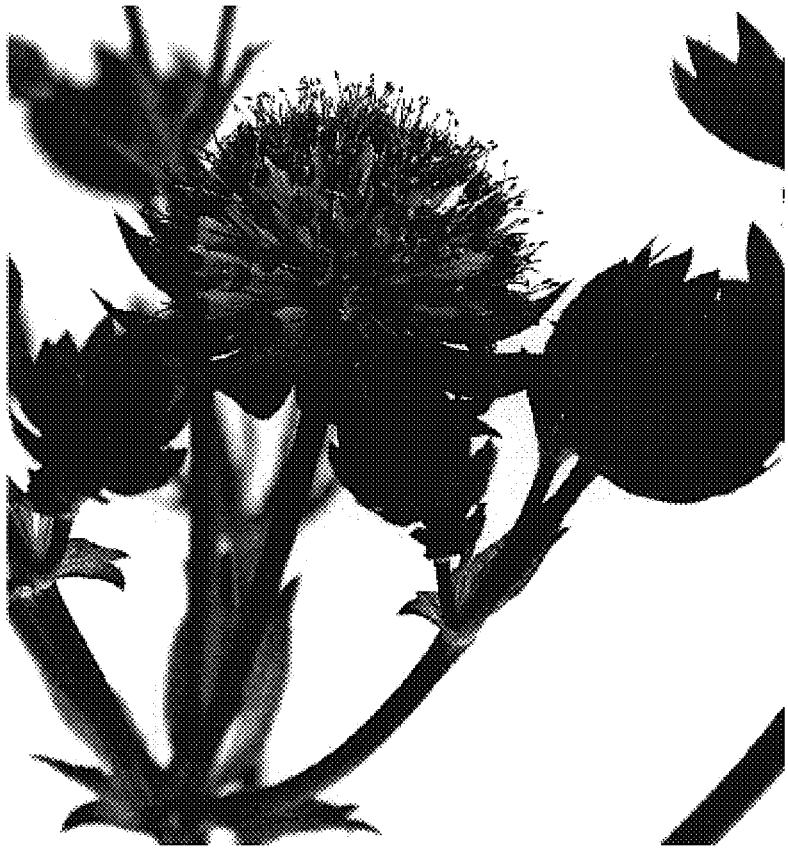
FIG. 2 shows a close-up of a mature inflorescence.
Figure 3:
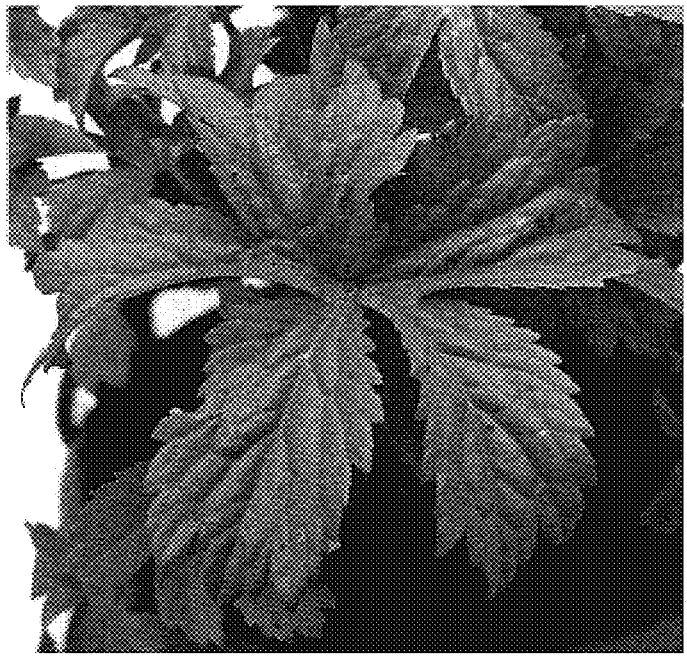
FIG. 3 shows a close-up a leaf.

The following detailed descriptions set forth the distinctive characteristics of 'Star of Fire'. The data which define these characteristics were collected from asexual reproductions carried out in De Hoef, The Netherlands. The plant history was taken on two-year-old plants grown from rooted cuttings in a field under normal outdoor light. Daytime temperatures ranged from 14° C. to 30° C. and night time temperatures ranged from 4° C. to 16° C. Plants were not pinched nor were growth retardants used. Color readings were taken under natural light. Color references are primarily to the R.H.S. Colour Chart of The Royal Horticultural Society of London (R.H.S.) (2001 edition).

DESCRIPTION OF THE NEW PLANT

Classification:
- *Family.*—Apiaceae.
- *Botanical name.*—*Astrantia* hybrid.
- *Common.*—Great masterwort.

Parentage:
- *Female parent.*—An unnamed selection of *Astrantia major* (unpatented).
- *Male parent.*—An unknown and unnamed selection of *Astrantia* (unpatented).

Plant:
- *Type.*—Herbaceous perennial.
- *Plant shape.*—Globular with flowering stems on the top.
- *Plant habit.*—Basal rosette with flowering stems growing from the base.
- *Vigor.*—Moderate; growth is about 15 cm per month.
- *Height.*—61.3 cm.
- *Diameter* (*spread*).—35.7 cm.

*Time to produce a finished flowering plant.*—About 19 weeks.
*Appropriate container systems.*—Use in pots or flowering beds.
*Garden performance.*—Highly tolerant to rain and wind; tolerant to high temperature of 30° C. and hardy to at least USDA Zone 6.
*Time to initiate roots.*—About 5 weeks.
*Root density.*—Dense.
*Root branching.*—Freely branching.
*Root color.*—Brown.
*Root thickness.*—Medium.
*Root texture.*—Moderately fibrous.

Branches:
*Branching.*—Basal branching; stems grow moderately free from a basal rosette.
*Number of flowering branches.*—3.
*Length of flowering branch.*—12.9 cm from the base to the lowest branching inflorescence.
*Diameter of flowering branch.*—0.6 cm.
*Internode length.*—10.1 cm.
*Appearance/shape.*—Rounded, slightly ribbed lengthwise, slightly glossy.
*Aspect.*—Slightly ribbed lengthwise.
*Strength.*—Strong.
*Color.*—RHS 144A (Yellow-green).
*Pubescence.*—Absent.

Leaves:
*Arrangement.*—Alternate, single.
*Quantity per branch.*—About 2; the whole plant has an average of 34 leaves, 28 of which are in the basal rosette.
*Shape.*—Palmately parted.
*Apex.*—Acute.
*Base.*—Hastate, the lower lobes are overlapping.
*Margin.*—Biserrate; average of 3 large teeth per 2 cm of margin; average of 3 smaller teeth per large tooth; the teeth are aristate.
*Pubescence.*—Absent.
*Color, immature leaf.*—Upper surface: RHS 143A (Green). Lower surface: RHS 143C (Green).
*Color, mature leaf.*—Upper surface: RHS 137A (Green). Lower surface: RHS 138B (Green).
*Length.*—Basal leaf: 10.8 cm. Stem leaf: 7.3 cm.
*Width.*—Basal leaf: 13.1 cm. Stem leaf: 9.4 cm.
*Texture.*—Smooth.
*Venation pattern.*—Laciniate.
*Vein color* (*both surfaces*).—RHS 145A (Yellow-green).
*Petiole.*—Basal leaf: Length: 15.4 cm. Diameter: 0.2 cm. Shape: Ovate. Height: 0.3 cm. Color: RHS 144A; base is RHS 187A to RHS 187B (Greyed-purple). Stem leaf: General: Stem leaf is sheathed. Length: 8.9 cm. Diameter: 0.4 cm. Height: 0.6 cm. Color: RHS 144A (yellow-green).
*Durability of foliage to stresses.*—High.

Flower bud:
*Length.*—0.7 cm.
*Diameter.*—0.15 cm.
*Shape.*—Obovate with a flattened top.
*Color.*—Between RHS 59A (Red-purple) and RHS 187B (Greyed-purple); apex is RHS 186B to RHS 186C (Greyed-purple); base is RHS 145B (Yellow-green).

Inflorescence:
*Shape/arrangement.*—Compound umbel.
*Height* (*including the peduncle*).—46.3 cm.
*Width.*—43.8 cm.
*Quantity of flowers per inflorescence.*—80 flowers per umbel; about 54 umbels per compound umbel.
*Flowering habit.*—Once per year, late spring into summer but continuous during that time.
*Quantity of flowers per flowering stem.*—4,000.
*Quantity of flower buds per flowering stem.*—4,000.
*Quantity of flowers and buds per plant.*—12,000.
*Time to produce flowers on the plant.*—Approximately 9 months (for field-grown plants).
*Rate of flower opening.*—Approximately 6% of flowers are open at once (central umbels) followed by secondary umbels; all flowers of an umbel open at the same time; the primary umbels open first, followed by the secondary umbels, tertiary umbels, etc.
*Fragrance.*—Very faint and relatively unpleasant.

Flowers:
*Type.*—Single.
*Aspect.*—Upright and upright-outward.
*Shape.*—Rotate.
*Diameter.*—0.4 cm.
*Height* (*depth*).—1.0 cm.
*Lastingness of flowers on the plant.*—12 days.
*Persistent or self-cleaning.*—Self-cleaning.

Petals:
*Quantity* (*per flower*).—5.
*Arrangement.*—Rotate and upright; petals are not fused.
*Surface.*—Dull and smooth.
*Size.*—Length: 0.2 cm. Width: 0.1 cm.
*Shape.*—Ovate, recurved.
*Apex.*—Narrow acute.
*Margin.*—Entire.
*Color, when opening* (*both surfaces*).—RHS 63C to RHS 63D (Red-purple).
*Color, when fully opened* (*both surfaces*).—RHS 63C to RHS 63D (Red-purple).

Calyx:
*Shape.*—Rotate, the sepals are upright.
*Length.*—0.25 cm.
*Diameter.*—0.2 cm.

Sepals:
*Arrangement.*—Rotate and upright.
*Quantity.*—5 sepals.
*Texture* (*both surfaces*).—Dull, smooth.
*Size.*—Length: 0.25 cm. Width: 0.06 cm (measured at base).
*Shape.*—Ovate.
*Apex.*—Broad acute.
*Base.*—Cuneate.
*Margin.*—Entire.
*Color, immature* (*both surfaces*).—RHS 143A (Green) with an RHS 59A to RHS 187B (Greyed-purple) tip.
*Color, mature* (*both surfaces*).—RHS N186C (Greyed-purple) with a lighter RHS 186A to RHS 186B (Greyed-purple) tip.

Bracts:
*General.*—A ring of bracts is placed under each umbel.
*Number.*—20.
*Shape.*—Elliptic to narrow obovate.
*Apex.*—Acute.
*Base.*—Attenuate.
*Margin.*—Entire.
*Length.*—2.0 cm.
*Width.*—0.5 cm.

*Texture.*—Dull and smooth.

*Color* (*both surfaces*).—Between RHS 59A and RHS N186D (Red-purple to greyed-purple) with RHS N186C (Greyed-purple) tips and main veins.

Pedicel:

*Length.*—1.0 cm.

*Diameter.*—0.03 cm.

*Angle.*—Central flowers straight upright; outer flowers at 90°.

*Color.*—RHS 63D (Red-purple).

*Strength.*—Strong.

Peduncle:

*Length.*—3.8 cm.

*Diameter.*—0.25 cm.

*Angle.*—Primary umbel straight upright; secondary umbels average angle of 40°.

*Color.*—Upper surface: Between RHS 186C and RHS 200A (Greyed-purple to brown). Lower surface: Between RHS 186C and RHS200A (Greyed-purple to brown) tinged with RHS 146A (Yellow-green).

*Strength.*—Strong.

Reproductive organs:

*Stamens.*—Quantity: 5.

*Anthers.*—Shape: Dorsifixed, elliptic. Size: Anther length: 0.1 cm. Filament length: 0.35 cm. Color: Anther: RHS 63C (Red-purple). Filament: RHS 63B (Red-purple).

*Quantity of pollen.*—Low.

*Pollen color.*—RHS 155A (White).

*Pistil.*—Pistil number: 2. Pistil length: 0.45 cm. Stigma shape: Club-shaped. Stigma color: RHS 63C (Red-purple). Style length: 0.4 cm. Style color: RHS 63C (Red-purple), lighter towards the base. Ovary color: RHS 193A to RHS 193B (Greyed-green).

Fruit and seed set: None.

Disease and insect resistance: No susceptibility to common diseases or pests has been observed.

COMPARISON WITH PARENTAL AND COMMERCIAL CULTIVARS

'Star of Fire' differs from the female parent, an unnamed and unpatented selection of *Astrantia major,* in that 'Star of Fire' has deep red flowers on dark peduncles while the female parent has lighter colored flowers on lighter colored peduncles. In addition, 'Star of Fire' has considerably larger inflorescences than the female parent.

'Star of Fire' differs from the *Astrantia* variety 'Florence' (U.S. Plant Pat. No. 18,478) in that 'Star of Fire' has an average plant height of 61.3 cm while 'Florence' has a plant height of 88 cm. In addition, 'Star of Fire' has a bract color of RHS 59A to RHS N186D with RHS 186C tips and main veins while 'Florence' has a bract color of RHS 65C to RHS 65D with RHS 137A tips and RHS 143A venation.

I claim:

1. A new and distinct cultivar of *Astrantia* plant as shown and described herein.

* * * * *